US011653950B2

United States Patent
Gambardella et al.

(10) Patent No.: US 11,653,950 B2
(45) Date of Patent: May 23, 2023

(54) DEVICE FOR CAESAREAN DELIVERY

(71) Applicant: LUMGI SAGL, Lugano (CH)

(72) Inventors: Luca Maria Gambardella, Massagno (CH); Umberto Botta, Magliaso (CH); Ginevra Licandro, Gnosca (CH)

(73) Assignee: LUMGI SAGL, Lugano (CH)

( * ) Notice: Subject to any disclaimer, the term of this patent is extended or adjusted under 35 U.S.C. 154(b) by 0 days.

(21) Appl. No.: 17/439,270

(22) PCT Filed: Mar. 27, 2020

(86) PCT No.: PCT/IB2020/052905
§ 371 (c)(1),
(2) Date: Sep. 14, 2021

(87) PCT Pub. No.: WO2020/201952
PCT Pub. Date: Oct. 8, 2020

(65) Prior Publication Data
US 2022/0142675 A1 May 12, 2022

(30) Foreign Application Priority Data

Apr. 2, 2019 (IT) .......................... 102019000004964

(51) Int. Cl.
*A61B 17/42* (2006.01)
(52) U.S. Cl.
CPC ........ *A61B 17/42* (2013.01); *A61B 2217/005* (2013.01)
(58) Field of Classification Search
CPC ... A61B 17/42; A61B 2217/005; A61B 17/32; A61B 2017/320052; A61B 2017/12004
See application file for complete search history.

(56) References Cited

U.S. PATENT DOCUMENTS

| 5,246,446 A | * | 9/1993 | Zweig | A61B 17/42 606/119 |
|---|---|---|---|---|
| 2013/0304080 A1 | | 11/2013 | Landry | |
| 2014/0309671 A1 | | 10/2014 | Basic et al. | |
| 2017/0014199 A1 | | 1/2017 | Schwartz et al. | |
| 2017/0265957 A1 | * | 9/2017 | Chua | A61B 50/30 |

FOREIGN PATENT DOCUMENTS

JP 2008-207020 A 9/2008

OTHER PUBLICATIONS

International Search Report and Written Opinion issued in corresponding International Application No. PCT/B2020/052905, dated Jul. 3, 2020, pp. 1-12.

\* cited by examiner

*Primary Examiner* — Timothy J Neal
*Assistant Examiner* — Andrew P. Restaino
(74) *Attorney, Agent, or Firm* — Carter, DeLuca & Farrell LLP

(57) ABSTRACT

Blood-flow reduction device (1) for Caesarean delivery operations, comprising a frame (2) defining internally an area (3) inside which a cut may be made along an incision line (L) on the uterus of a patient giving delivery. The blood-flow reduction device comprises at least one gripping means (4) for exerting a pressure on the patient giving birth using the frame (2) and reducing the blood flow in the area (3).

15 Claims, 2 Drawing Sheets

DEVICE FOR CAESAREAN DELIVERY

CROSS REFERENCE TO RELATED APPLICATIONS

This application is a national stage application of International Application No. PCT/IB2020/052905, filed Mar. 27, 2020, which claims the benefit of and priority to Italian Patent Application No. 102019000004964, filed Apr. 2, 2019, the entire contents of each of which are hereby incorporated by reference herein.

FIELD OF APPLICATION

The present invention relates to a device for Caesarean delivery operations.

In particular, the present invention relates to a device of the aforementioned type, able to limit the problems resulting from sudden haemorrhages during Caesarean delivery operations.

PRIOR ART

As is known, a Caesarean delivery operation is generally carried out by two surgeons and a surgical assistant. Initially an anaesthetic is given to the patient giving birth and, after disinfecting the abdomen, an incision is made in the skin (epidermis, dermis and hypodermis) on the abdomen, about two centimetres above the pubis, as schematically shown in FIGS. 1 and 2.

The incision in the skin extends along a horizontal line L. Only in rare cases is a longitudinal incision required, namely an incision extending from the navel to the pubis.

The incision is made not only in the skin, but also in the muscle tissue, i.e. the connective tissue which covers and supports with a trophomechanical function the muscles which are instead not cut, but separated. The peritoneum, a serous mesothelial membrane which encloses all the organs in the abdomen, is also cut and finally the uterus is cut. In other words, the Caesarean delivery operation involves making several cuts at different depths. Following breakage of the amniotic sac the surgeon may reach the baby, gripping its head, feet or buttocks.

In some patients giving birth, the aforementioned operations may be extremely complicated, to the point of putting at risk the life of the baby to be delivered and/or of the patient herself. For example, if there anatomical or physiological variations of the blood vessels (such as varicose veins or a high blood pressure and flow), execution of the cuts, especially deeper cuts, becomes more problematic, with consequences which are unpredictable and/or difficult to manage. For example, immediately after a cut which involves severing of the varicose veins, an abundant and substantially uncontrollable haemorrhage may occur, this literally flooding the area where the surgeon must operate, reducing or completely blocking his/her vision of the underlying tissues and therefore preventing him/her from proceeding with the operation and reaching the baby quickly. In such cases a danger situation arises for the patient giving birth, owing to the loss of blood, with the consequent risk of complications.

These situations are extremely difficult and delicate because they result in the need to conclude the operation very rapidly in order to prevent life-threatening blood losses. Even the most skilled and expert surgeons may find themselves in very serious difficulty when performing these operations, since the devices which are currently available for the surgical assistant or surgeon are unable to solve the abovementioned problems, i.e. limit the complications resulting from the immediate and uncontrollable loss of a large amount of blood. Instead it may happen that this escaping blood may even strike the surgeons and the assistant, preventing the latter also from correctly assisting the surgeon.

The technical problem forming the basis of the present invention is to devise a device which is able to solve all the abovementioned problems of a Caesarean delivery and in particular a device intended to block substantially or at least reduce significantly the haemorrhage and the liquid blood flow in the operating zone, at least until the surgeon is able to pass through the different layers of the abdomen which are accessible following the cuts performed, thus being able to reach the baby to be delivered and complete the operation in safety and extremely rapidly.

SUMMARY OF THE INVENTION

The idea underlying the present invention is that of providing a blood-flow reduction device which can be applied to the uterus of a patient giving birth before the uterotomy and which leaves the surgeon the space necessary for forming the cut through which to access the baby to be delivered, but which at the same time blocks the blood flow in the area of the cut immediately after the cut has been performed, thus allowing safe, rapid and effective gripping and manoeuvring of the newly born baby.

Based on the present invention, the aforementioned technical problem is solved by a blood-flow reduction device for Caesarean delivery operations, comprising a frame defining internally a free area inside which a cut can be made along an incision line of the uterus of a patient giving birth, and at least one gripping means on the frame for exerting a pressure with the frame on the patient giving birth, before making the cut, and thus reducing the blood flow towards the area inside the frame, immediately after cutting. According to the present invention, the frame is a closed ring and encloses the area so that the pressure of the frame on the patient giving birth may reduce, during use, the blood flow within the closed area inside the frame as a result of the cut and thus prevent the area from being covered by the blood, making it difficult for the surgeon to operate efficiently.

Essentially, the frame is placed in pressing contact with the body of the patient giving birth, for example over the varicose veins which must be severed before the cut, in order to stem the blood flow from said veins towards the area inside the frame, where the surgeon must have access to the uterus, once the veins have been cut, and thus allow time to make contact with the baby to be delivered without having to manage a haemorrhage at the same time.

By means of the pressure exerted with the frame on the patient, around the incision line, it is possible to constrict the severed blood vessels or at least reduce significantly the blood flow from these vessels, since they remain temporarily compressed underneath the frame, leaving the surgeon free to operate in the area inside the frame, which advantageously remains clean and visible.

The frame is placed in contact with the patient before the incision is made and may remain in contact with her also after the incision has been made, still in contact with the uterus, until the surgeon manages to locate and grip with his/her hands the head and the feet of the baby to be delivered, via the cut made in the uterus itself. Then, after the surgeon has made contact with the baby to be delivered, the blood-flow reduction device may be removed.

So as not to loose contact with the baby during the removal of the blood-flow reduction device, after the surgeon has inserted one or more fingers inside the incision in the uterus through the opening in the centre of the frame, he/she may use a finger or fingers of the other hand to locate the baby, inserting however the fingers of the other hand inside the incision in the uterus without passing through the opening in the centre of the frame, i.e. by passing the fingers of the second hand underneath the frame. During this operation it is possible to cooperate with the surgical assistant so that the pressure of the frame on the patient's body is lessened slightly, thus allowing the fingers of the second hand to enter rapidly and make immediate contact with the baby to be delivered.

According to another aspect of the present invention, owing to a particular structure of the frame, it is possible to avoid interrupting the contact between the fingers of the surgeon's hand which have been inserted through the area inside the frame, and the baby to be delivered, during removal of the frame.

In particular, the frame may be a closed ring. However, this ring may be opened, for example by means of a removable or hinged portion, for example in a plane transverse to the fingers of the hand, thus allowing the frame to be rotated around the fingers.

According to an aspect of the present invention, the frame has an elongated, preferably oval, quadrangular or polygonal form.

Preferably, two distal handles are situated on opposite portions of the frame arranged close together. Obviously, the frame may also have other forms, for example a circular form. Similarly, only one handle or more than two handles may be provided.

The opening in the frame has a diameter or width of between 5 and 10 cm. Therefore, it is sufficient for the cut formed in the uterus to allow the surgeon to touch the baby with a finger in order to avoid dangerous delays during the operation. Therefore, once the surgeon has inserted a finger or several fingers through the cut in the uterus, making contact with the baby, even before the baby has been extracted or completely extracted from the uterus, the blood-flow reduction device may be removed.

Using the handles, the frame may be pressed against the patient's body.

Preferably, according to an embodiment of the invention, the structure is associated with an aspirator which is able to remove the liquid blood resulting from severing of the vessels during the incision.

Advantageously according to this embodiment, not only is it possible to reduce or block the haemorrhage resulting from the vessels upstream and downstream of the blood-flow reduction device, but the liquid blood released by the blood vessels severed in the cutting area may also be removed.

In a ring-shaped frame, the ring may have a C-shaped cross-section with the opening of the C section directed towards the centre of the frame, i.e. towards the cutting area. A side wall of the C section is intended to remain in contact with the patient giving birth and an opposite side wall may form a connection for the aspirator.

Preferably, the aspirator is applied onto a connection arranged spaced from the frame handles.

According to an embodiment, the handles are formed as one piece with the frame.

According to another embodiment, at least one handle can be removed from the frame. In particular, the handle may form part of the frame, for example part of the closed ring. Advantageously, removal of the handle involves opening of the ring; this configuration also allows removal of the frame without the surgeon having to remove his/her hands from the cutting area on the uterus, around which the structure is initially positioned.

Preferably, the handles are aligned with the incision line. For example, the first and second handles are angularly spaced on the frame at an angle greater than 90°, preferably equal to 120°.

Special features are provided in order to ensure the complete safety of the patient giving birth. For example, the structure comprises a surface lining intended to make pressing contact with the uterus, this lining being biocompatible, compressible and sterilizable. The structure does not have sharp corners.

Further characteristic features and advantages of the present invention will become clear from an embodiment thereof, provided purely by way of a non-limiting example, with reference to the accompanying drawings.

DETAILED DESCRIPTION

With reference to the attached figures, examples of embodiment of a blood-flow reduction device for Caesarean delivery operations according to the present invention are described below.

Figure 1:
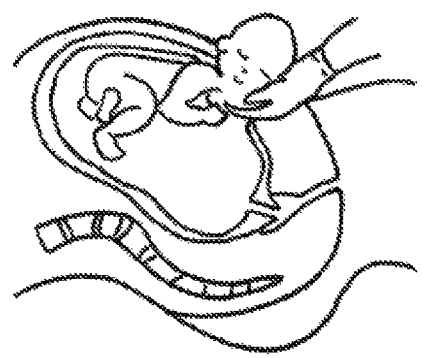
FIG. 1 shows a schematic view of a patient giving birth, a newly born baby and the hand of a surgeon in the cutting area of a Caesarean delivery.
Figure 2:
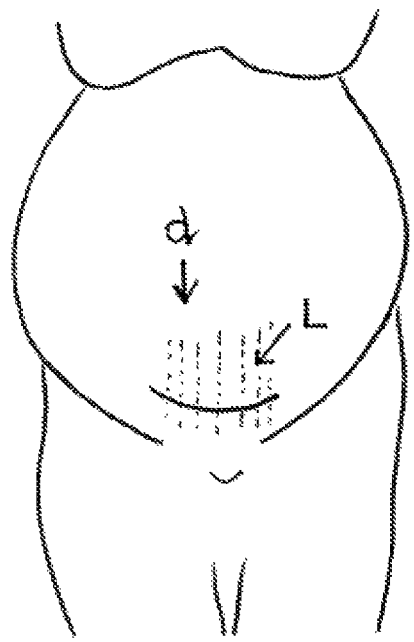
FIG. 2 shows a schematic view of the cutting line of a Caesarean delivery.
Figure 3:
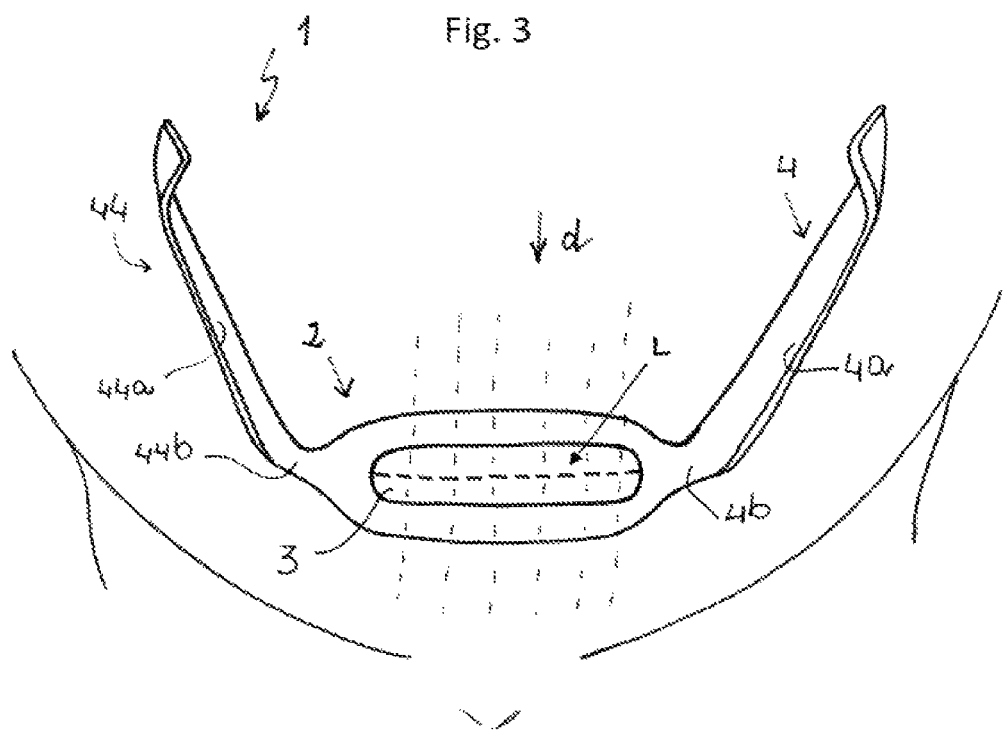
FIG. 3 shows a schematic view of a blood-flow reduction device for a Caesarean delivery, according to the present invention.

The blood-flow reduction device is intended to be used during execution of the incision on the patient giving birth, as schematically shown in FIG. 3, along a line L which is normally horizontal or—more rarely—longitudinal (head-to-foot direction), passing through the skin, and at a deeper level, through the muscle fibre, peritoneum and uterus.

In particular, the blood-flow reduction device is intended to be applied to the patient giving birth with the aim of reducing the flow from the blood vessels when it is envisaged that the incision may result in an immediate and sudden loss of a very large amount of blood, owing to particular physiological parameters of the patient giving birth, such as high blood pressure or specific anatomical conditions, such as the presence of varicose veins along the incision line L, or other complications.

The aforementioned physiological and anatomical conditions may be measured before programming the Caesarean delivery operation, by means of an ultrasound scan or other instrumental detection methods, thus allowing the surgeon to plan application of the blood-flow reduction device together with his/her team, before carrying out the operation. Obviously, a surgeon may employ the blood-flow reduction device according to the present invention for all the Caesarean delivery operations for which he/she is responsible, including those where there is an unpredictable risk, namely operations where there are no anatomical or physiological conditions leading one to assume that there will be an exceptional blood loss as a result of the incision.

The incision line shown in FIG. 3 is schematically indicated by L and is located a few centimetres above the pubis of the patient giving birth. Entirely by way of example, FIG. 3 shows a number of broken lines, extending transversely with respect to the line L, which indicate possible varicose veins, i.e. blood vessels which have a cross-section anatomically larger than normal, and which therefore may be the cause of potential complications after severing. Obviously, in the human body these veins may extend with a geometry different from that shown by way of example in FIG. 3 and therefore intersect the cutting line L differently from that shown. Similarly, the complications may arise from blood vessels which have a cross-section which is normal, but which are affected by a high blood pressure.

The blood-flow reduction device 1 is provided with a frame 2 defining internally a free area 3 inside which the cut may be performed along the incision line L of the uterus. The frame 2 is intended to close off the varicose veins or the blood vessels after the incision has been made, or at least reduce significantly the blood flow, preventing the area 3 where the surgeon must operate from being obscured by the blood. In other words, the frame 2 is intended to be kept in pressing contact with the body of the patient and to remain in contact with it, including the uterus, during cutting, mutually constricting the varicose veins or other venous vessels, upstream and downstream of the line L.

When the uterus has been cut, by about 2 centimetres, the surgeon may insert a finger inside the uterus and attempt to make contact with the baby, locating the head, a foot or the buttocks, while a surgical assistant continues to keep the frame 2 in contact with the patient.

In order to exert a pressure sufficient to interrupt the blood flow, it is envisaged that the blood-flow reduction device may be provided with a gripping means 4. The pressure is applied, preferably from the start of the cutting operation and is maintained at least until the surgeon is able to make contact with the baby to be delivered. Only when the surgeon makes contact with the baby, identifying its position in the uterus, is the pressure on the frame released; in fact, after gripping the baby, the surgeon may proceed relatively quickly to extract it and immediately deal with stopping the bleeding of the patient, even if it is copious.

In the example shown in FIG. 3, the gripping means 4 is composed of a pair of handles 4, 44 which are formed as one piece with the frame 3, which is for example a closed ring, having an elliptical form. The handles 4, 44 are situated on the portions of the elliptical ring which are spaced furthest apart from each other. During use, these portions of the elliptical ring may be substantially aligned with the line L; a surgical assistant may take hold of the handles 4, 44, while remaining to one side of the patient giving birth and press with a suitable force the frame 3 on the patient, without disturbing the surgeon, who instead remains positioned between the legs of the patient and is able to concentrate on cutting and the following steps.

The frame 2 may be substantially flat and the handles may be perpendicular to the flat frame or spaced angularly with respect to the plane of the flat frame, at an angle greater than 90°, for example 120°.

The example provided with reference to FIG. 3 does not however limit the scope of protection of the present invention. In fact, the frame 2 may have a circular, square or polygonal form; moreover, for each of these forms, the frame 2 may be closed ring, an open ring or a ring which can be opened. Still according to variations of embodiments of the present invention, the handles may be situated on the portions of the frame which are arranged close together, for example on portions of an elliptical shaped frame arranged close together.

Figure 4:
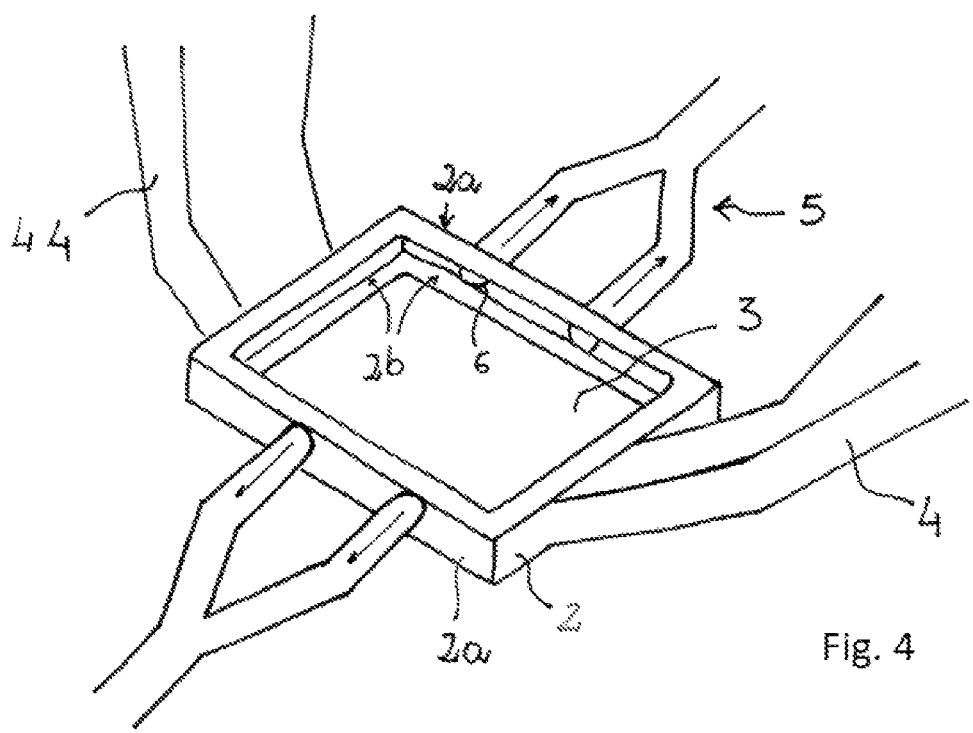
FIG. 4 shows a schematic view of a blood-flow reduction device for a Caesarean delivery, according to a variation of embodiment of the present invention.

In the example of embodiment shown in FIG. 4, the frame 2 is rectangular and the handles 4, 44 are located on the opposite smaller sides of the frame 2.

In particular, according to one aspect of the present invention, again described with reference to FIG. 4 only by way of example, the frame 2 is further associated with an aspirator 5 which is able to remove from the area 3 the liquid blood dispersed by severing of blood vessels along the incision line L. In fact, even of the frame 2 is kept pressed against the patient giving birth before performing the cut and thus also blocking off the flow of the blood vessels below the frame 2, the blood which is inside the part of the vessels extending inside the area 3 of the frame 2 cannot be prevented from at least partially flowing out into the area 3, after cutting, thus obscuring the area 3 and reducing the visibility. Advantageously, the aspirator 5 removes the blood from the area 3, keeping it clean and clearly visible.

In the example shown in FIG. 4, the frame 2 has a first surface (in this case with a rectangular shape) intended to remain in contact with the body of the patient giving birth, a second surface (or side 2a), for example situated at 90° with respect to the first surface, and a third surface, parallel to the first surface. In particular, the first, second and third surfaces of the frame 2 form a C-shaped section having an opening directed towards the area 3. The first surface, and preferably also all the remaining surfaces of the frame, is/are lined with a biocompatible and sterilizable material; moreover the frame 2 does not have sharp corners.

The flank 2a is provided with connections 6 for the aspirator 5, which are for example situated on the sides of the frame 2 adjacent to the smaller sides on which the handles 4, 44 are mounted. The ducts of the aspirator 5 supply the blood sucked from the area 3 towards a collection tank (not shown), thus cleaning the area 3 of the blood.

The suction ducts, according to another aspect which falls within the scope of protection of the present invention, may be formed by the handles 4, 44. For example, the proximal handle 4b close to a first handle 4 may emerge in the area 3 towards the centre of the frame 2. Similarly, the second handle 44 may have a respective proximal connection piece 44b, close to the frame 2, which emerges in the area 3, on a side of the frame 2 opposite to the side where the proximal connection piece 4b of the first handle 4 emerges. FIG. 4 therefore shows four aspiration ducts (and therefore four respective connection pieces connected to the frame), but the scope of protection of the present invention may also include devices with a single aspiration duct and with two or more aspiration ducts, optionally only two ducts which are incorporated in the handles.

According to another aspect of the present invention the frame 2 is a ring which can be opened. In particular, two components of the frame 2 (not shown) may be engaged and disengaged. When the components are engaged, the frame 2 forms a closed ring and when the components are disengaged the frame 2 forms an open ring. Advantageously, according to this embodiment, the removal of the frame 2 from the patient's body is facilitated when the surgeon has made contact with the baby inside the uterus, since the frame 2 may be opened by moving the disengageable components around the surgeon's arm, without the surgeon removing the finger or fingers from the uterus. For example, the disengageable components are formed by a fixed portion of the frame and by a movable portion, the movable portion being rotatable about a hinge of the frame 2. Other engaging and disengaging means, preferably of the quick release type, may be used in order to speed up removal of the frame 2 from the patient giving birth without interfering with the surgeon's arm.

The advantages of the blood-flow reduction device according to the present invention may be briefly summarised below.

The device prevents uncontrollable blood haemorrhages and flooding of the area where the surgeon must operate and blocking of his/her vision of the tissues underneath the cut. The device allows the surgeon to perform the Caesarean delivery operation rapidly and reach the baby quickly. Risk situations both for the patient giving birth and for the baby being delivered are thus avoided.

The invention claimed is:

1. A blood-flow reduction device for Caesarean delivery operations, comprising:
    a frame, defining internally an area inside configured for a cut to be made along an incision line of a uterus of a patient giving birth; and
    at least one gripping means configured for exerting a pressure with the frame on the patient giving birth, the at least one gripping means comprising at least one first handle with a proximal connection piece and a distal connection piece, the at least one first handle forming an aspiration duct of an aspirator emerging inside the area towards a center of the frame,
    wherein the frame is a closed ring and encloses the area so that the pressure of the frame on the patient giving birth reduces blood flow within the closed area inside the frame as a result of the cut.

2. The device according to claim 1, wherein the frame is associated with the aspirator configured to remove liquid blood from the area which is dispersed as a result of cutting of blood vessels along the incision line.

3. The device according to claim 2, wherein the frame has a C-shaped cross-section with an opening directed towards the area towards the center of the frame.

4. The device according to claim 2, wherein the frame is provided with a connection for the aspirator.

5. The device according to claim 4, wherein the ring can be opened.

6. The device according to claim 1, wherein the at least one gripping means comprises a second handle having a respective proximal connection piece, situated opposite the proximal connection piece of the at least one first handle, and a distal connection piece.

7. The device according to claim 6, wherein the frame has an elongated, oval, quadrangular or polygonal form, and the distal connection pieces are situated on opposite portions of the frame arranged close together.

8. The device according to claim 1, wherein said at least one first handle is formed as one piece with the frame.

9. The device according to claim 6, wherein the at least one first handle and the second handle are formed as one piece with the frame.

10. The device according to claim 9, wherein at least the second handle can be removed from the frame.

11. The device according to claim 6, wherein the at least one first handle and second handle are configured to be aligned along the incision line and are orthogonal to the area.

12. The device according to claim 6, wherein the at least one first handle and second handle are arranged spaced from each other on the frame at an angle greater than 90°.

13. The device according to claim 1, wherein the frame comprises a surface lining configured to make pressing contact with the uterus, the surface lining being biocompatible and sterilizable.

14. The device according to claim 1, wherein the frame does not have sharp corners.

15. The device according to claim 6, wherein the at least one first handle and second handle are arranged spaced from each other on the frame at an 120° angle.

* * * * *